(12) United States Patent
Stroumpoulis et al.

(10) Patent No.: US 8,961,474 B2
(45) Date of Patent: Feb. 24, 2015

(54) SYRINGE

(75) Inventors: Dimitrios Stroumpoulis, Goleta, CA (US); Christopher S. Mudd, Goleta, CA (US)

(73) Assignee: Allergan, Inc., Irvine, CA (US)

(*) Notice: Subject to any disclaimer, the term of this patent is extended or adjusted under 35 U.S.C. 154(b) by 450 days.

(21) Appl. No.: 12/968,576

(22) Filed: Dec. 15, 2010

(65) Prior Publication Data

US 2011/0166531 A1 Jul. 7, 2011

Related U.S. Application Data

(60) Provisional application No. 61/292,370, filed on Jan. 5, 2010.

(51) Int. Cl.
*A61M 5/315* (2006.01)
*A61M 5/19* (2006.01)

(52) U.S. Cl.
CPC .............. *A61M 5/19* (2013.01); *A61M 5/31596* (2013.01); *A61M 2005/31508* (2013.01); *A61M 2005/31598* (2013.01)
USPC ....................................................... 604/220

(58) Field of Classification Search
USPC .......... 604/220, 181, 187, 191, 207–211, 218
See application file for complete search history.

(56) References Cited

U.S. PATENT DOCUMENTS

| 4,753,536 | A | | 6/1988 | Spehar et al. |
| 4,813,433 | A | * | 3/1989 | Downey ........................ 600/578 |
| 5,445,614 | A | * | 8/1995 | Haber et al. ..................... 604/89 |

| 2007/0073267 | A1 | | 3/2007 | Muller |
| 2009/0101670 | A1 | | 4/2009 | Restive et al. |
| 2009/0131886 | A1 | | 5/2009 | Liu et al. |
| 2009/0287161 | A1 | * | 11/2009 | Traub et al. ................... 604/208 |

FOREIGN PATENT DOCUMENTS

| EP | 1093826 | 4/2001 |
| WO | 9422507 | 10/1994 |
| WO | 2005095225 | 10/2005 |

OTHER PUBLICATIONS http://www.drugs.com/pro/lupron-depot.html, Revised Feb. 2011, Abbott Laboratories.

* cited by examiner

*Primary Examiner* — Aarti B Berdichevsky
*Assistant Examiner* — Bradley Osinski
(74) *Attorney, Agent, or Firm* — Linda Allyson Nassif

(57) ABSTRACT

A syringe is disclosed. The syringe may include a syringe body with a fluid chamber, the syringe body having a distal end and a proximal end, with an extrusion opening at the proximal end; a dividing wall disposed within the fluid chamber, defining a first fluid chamber and a second fluid chamber, the first fluid chamber and the second fluid chamber in communication with the extrusion opening; a first plunger disposed in a distal end of the first chamber, the first plunger including a first locking mechanism configured to prevent the first plunger from sliding away from the proximal end of the syringe body, when the first plunger is in a first initial position and the second plunger is being depressed; and a second plunger disposed in a distal end of the second chamber, the second plunger including a second locking mechanism configured to prevent the second plunger from sliding away from the proximal end of the syringe body when the second plunger is in a second initial position and the first plunger is being depressed.

6 Claims, 7 Drawing Sheets

SYRINGE

RELATED APPLICATION

This application claims priority to and the benefit of U.S. Provisional Patent Application No. 61/292,370, filed on Jan. 5, 2010, the entire disclosure of which is hereby incorporated by reference herein.

BACKGROUND

A number of medical applications require the injection of significant amounts of material. For example, one such application is the injection of dermal fillers to correct facial wrinkles or folds. In such a procedure, a possibly significant quantity of dermal filler material is injected under the skin using a syringe. In addition, the material injected may have a higher viscosity than the substances typically injected by syringe. For example, some dermal fillers may include gels, such as a gel made of hyaluronic acid. Traditional syringes and the plunger rods used with such syringes present a number of problems when used for such applications. For instance, in order to accommodate significant volumes of material, such syringes must typically have either a large length or cross-sectional area. Syringes with larger cross-sectional areas are often not practical, however, because the extrusion force required when operating a syringe increases with the cross-sectional area, this may be particularly problematic when injecting viscous fluids. Increasing the length of a traditional syringe, however, may significantly increase the overall length of the device, as a longer plunger may also need to be used, which may reduce the user's comfort and control during use. Accordingly, example embodiments provide improved syringe and plunger devices which may address a number of the shortcomings of traditional devices.

SUMMARY

Example embodiments described herein provide a syringe, which may include a syringe body with a fluid chamber, the syringe body having a distal end and a proximal end, with an extrusion opening at the proximal end; a dividing wall disposed within the fluid chamber, defining a first fluid chamber and a second fluid chamber, the first fluid chamber and the second fluid chamber in communication with the extrusion opening; a first plunger disposed in a distal end of the first chamber, the first plunger including a first locking mechanism configured to prevent the first plunger from sliding away from the proximal end of the syringe body, when the first plunger is in a first initial position and the second plunger is being depressed; and a second plunger disposed in a distal end of the second chamber, the second plunger including a second locking mechanism configured to prevent the second plunger from sliding away from the proximal end of the syringe body when the second plunger is in a second initial position and the first plunger is being depressed.

In some example embodiments, the first locking mechanism may include a first locking wing formed at a proximal end of the first plunger; and a first groove formed in the distal end of the first fluid chamber; where the first locking wing may be positioned to engage in the first groove when the first plunger is in the first initial position.

Some example embodiments may also include a third locking mechanism configured to prevent the first plunger from sliding away from the proximal end of the syringe body, when the first plunger is in a first final position and the second plunger is being depressed; and a fourth locking mechanism configured to prevent the second plunger from sliding away from the proximal end of the syringe body, when the second plunger is in a second final position and the first plunger is being depressed.

In some example embodiments, the third locking mechanism may include a third locking wing formed at a distal end of the first plunger; and a third groove formed in a distal end of the first fluid chamber; where the third locking wing may be positioned to engage in the third groove when the first plunger is in the first final position.

In some example embodiments, the first groove may be the third groove. In other example embodiments the first groove may be distinct from the third groove. In still other example embodiments, the first locking wing may be a directional locking wing or the third locking wing may be a directional locking wing.

In some example embodiments, the first fluid chamber and the second fluid chamber may have a semi-circular cross-section. In other example embodiments, the first fluid chamber and the second fluid chamber may have a rectangular cross-section.

Other example embodiments may provide a syringe, which may include a syringe body with a fluid chamber, the syringe body having a distal end and a proximal end, with an extrusion opening at the proximal end; an outer plunger disposed in the distal end of the fluid chamber, the outer plunger having a bore running from a distal end to a proximal end; and an inner plunger slidably disposed in the bore.

Some example embodiments may also include a first locking mechanism configured to prevent the inner plunger from sliding relative to the syringe body when the inner plunger is in an initial position and the outer plunger is being depressed.

Some example embodiments may also include a first slot in the outer plunger, extending a portion of the length of the outer plunger from the distal end to the proximal end; where the first slot may be configured to allow the outer plunger to slide relative to the inner plunger and the syringe body when the first locking mechanism is engaged.

In some example embodiments, the locking mechanism may include a first locking arm disposed on the inner plunger near a proximal end of the inner plunger; and a first groove disposed within the syringe body near the distal end of the syringe body; where the first locking arm may be configured to engage in the first groove, when the inner plunger is in the initial position, passing through the first slot.

Some example embodiments may also include a second locking mechanism, configured to prevent the outer plunger from sliding relative to the syringe body when the outer plunger is in a final position and the inner plunger is being depressed.

In some example embodiments, the second locking mechanism may include a first locking tab disposed on the outer plunger near the distal end of the outer plunger; and a second groove disposed within the syringe body near the distal end of the syringe body; where the first locking tab may be configured to engage in the second groove, when the outer plunger is in the final position.

In some example embodiments, the first groove may be the second groove. In other example embodiments, the inner plunger and the outer plunger may have circular cross-sections. Some example embodiments may also include an outer plunger tip attached to the outer plunger; and an inner plunger tip attached to the inner plunger; where the inner plunger tip may be shaped to fit within a hole passing through the outer plunger tip.

In some example embodiments, the outer plunger tip may have a ring shape; and the inner plunger tip may have a disk shape.

BRIEF DESCRIPTION OF THE DRAWINGS

The present invention will be more readily understood from a detailed description of example embodiments taken in conjunction with the following figures.

DETAILED DESCRIPTION

Example embodiments of the invention generally relate to a new syringe system designed to dispense large volumes of fluid, while minimizing the force of extrusion and length of the device. Such example embodiments may, for example, be used in the administration of gels that can have cosmetic or medical applications.

Most current syringes are designed to dispense low viscosity fluids through a fine needle with minimum extrusion force. Higher viscosity fluids (e.g. dermal fillers) can also be dispensed with the current design, however at a considerably higher extrusion force. This can result in injection fatigue, as physicians are often required to perform numerous injections on a daily basis. In some other instances, high extrusion force can result in needle disengagement and possibly patient injury. Example embodiments, however, provide a syringe device reduces the extrusion force required, e.g., to extrude highly viscous fluid through a fine needle, while maintaining the same fill volume.

As an initial matter, the extrusion force required to maintain a constant flow of a Newtonian fluid through a tube with a constant circular cross-section is governed by the Hagen-Poiseuille equation:

$$F = A \cdot \Delta P = \pi r^2 \cdot \frac{8\mu L Q}{\pi r^4} = \frac{8\mu L Q}{r^2},$$

where:
ΔP is the pressure drop required to maintain a constant volumetric flow rate Q,
μ is the dynamic viscosity,
L is the length of the tube, and
r is the radius of the tube.

This general equation can be applied to a needle of length $L_n$ and radius $r_n$ $$F_n = \frac{8\mu L_n Q}{r_n^2}$$

This force must be applied to a cross-sectional area in the entrance of the needle to maintain a constant flow rate Q. The corresponding force on a cross-sectional area in the syringe can be calculated by assuming zero pressure drop in the syringe and equating the pressure in the entrance of the needle with the pressure in the syringe:

$$F_s = F_n \frac{A_s}{A_n} = \frac{8\mu L_n Q A_s}{\pi r_n^4}$$

where:
$A_s$ is the cross-sectional area of the syringe, and
$A_n$ is the cross-sectional area of the needle.

This is a simplified equation that assumes that the bottleneck of the process is the needle (where the majority of the extrusion energy is lost) and neglects entrance losses as the flow transitions from the syringe to the needle as well as losses in the syringe. According to this equation the extrusion force for a given flow rate Q is proportional to the length of the needle $L_n$, the viscosity of the fluid μ, and the cross sectional area of the syringe $A_s$, and inversely proportional to the 4th power of the needle radius $r_n$.

For a given fluid, needle, and flowrate, the only parameter that is left to control the extrusion force is the syringe cross-sectional area. Minimizing that parameter can reduce the force required to extrude a viscous solution through a fine needle. However, there is a limit on how much this area can be reduced, which is primarily determined by the fill volume of the syringe. As the syringe diameter decreases, the length of the syringe has to increase to accommodate the fixed volume of fluid. Increasing the length of the syringe, however, can result in practical issues, e.g. reduced functionality, ergonomics considerations, and less control over the needle that can not only cause physician discomfort, but ultimately affect the patient's safety.

Example embodiments may resolve these problems by, for example, providing dual/multi-chamber and/or dual/multi-plunger devices designed to reduce the force required to extrude a fluid through a fine needle while maintaining the same fill volume and length as a conventional syringe. In some example embodiments, such an effect is achieved by splitting a single syringe chamber into two or more chambers of equal or different cross-sectional areas and attaching one plunger to each chamber. The fluid is then extruded by applying force to the first plunger until it moves all the way through the first chamber and locks in the end position and then by applying force to the second plunger and so on until all the fluid is dispensed. In such example embodiments, all chambers merge into a single needle at the end of the device proximal to the point of injection (the terms proximal and distal, as used herein, are to be understood in relation to the point of injection during use). In other example embodiments, a single chamber may be provided with a dual/multi-plunger set-up, achieving a similar reduction in extrusion force.

Figure 1:
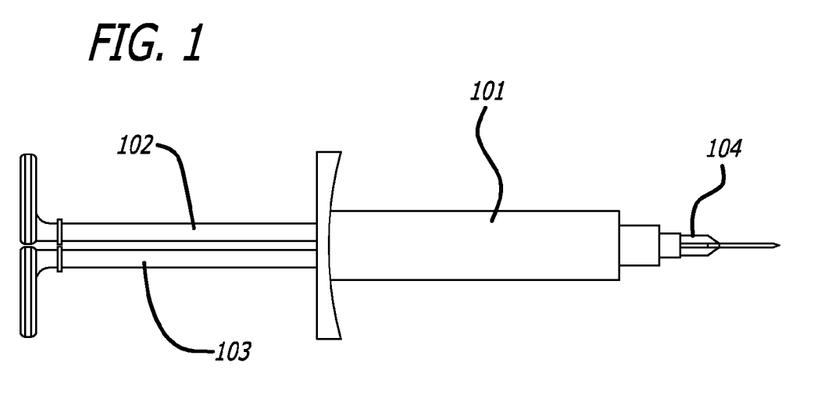
FIG. 1 illustrates an example dual-chamber/dual-plunger syringe in accordance with an example embodiment.

An example syringe and plunger device in accordance with an embodiment is shown in FIG. 1. As illustrated, the example device may have a syringe body 101 and a plurality of plungers 102, 103. The syringe body 101 may be shaped substantially like a conventional syringe. For instance, the syringe body 101 may be cylindrical, may have a proximal end, which may include an opening for extruding the injectable material contained in the syringe, and may also include an attachment point for attaching a needle 104, e.g. a luer, or may have an integrated needle 104. In addition, the syringe body 101 may also include finger grips 105, which may be used like the finger grips of a convention syringe, allowing a user to apply pressure to the plunger rods 102, 103.

In example embodiments, the syringe chamber may be divided into multiple chambers by a dividing wall. For example, the depicted syringe body 101 may be divided into two chambers, where each chamber may have a half-cylinder shape, though other shapes are also usable, e.g., chambers with the shape of a rectangle or other polygon, or of an oval, may also be used. The dividing wall may extend the length of the syringe 101 up to the point at which it meets the needle opening, or syringe luer, etc. In such embodiments, a plunger 102, 103, shaped to match the chambers, may be inserted into to the distal end of each chamber. Such plungers may be shaped generally in the form of a rod, and may have a plunger tip at a proximal end and a thumb grip at a distal end.

Figure 2:
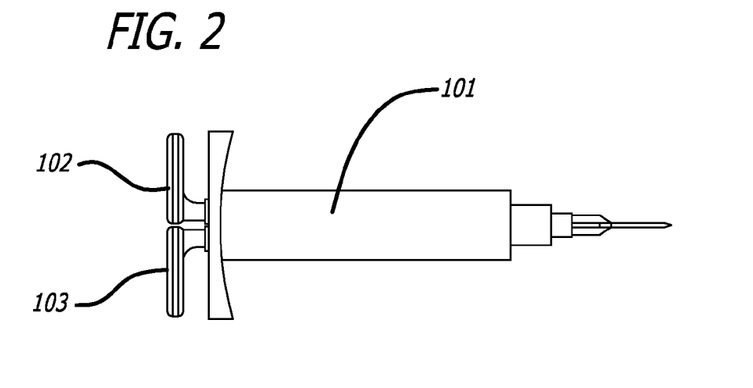
FIG. 2 illustrates an example dual-chamber/dual-plunger syringe in accordance with an example embodiment.

It is noted that FIG. 1 illustrates both plungers 102, 103 in their initial positions. That is, neither plunger 102, 103 has been pushed into the syringe body 101 at this point. FIG. 2 illustrates the final position of the device once all the material has been extruded. To use the device, a force may be applied to the first plunger 102 until all material in the first chamber is extruded and the plunger is locked in the final position. Force may then be applied to the second plunger 103 until all the material in the second chamber is extruded through the same needle 104 and the plunger 103 is locked in the final position.

Figure 3A:
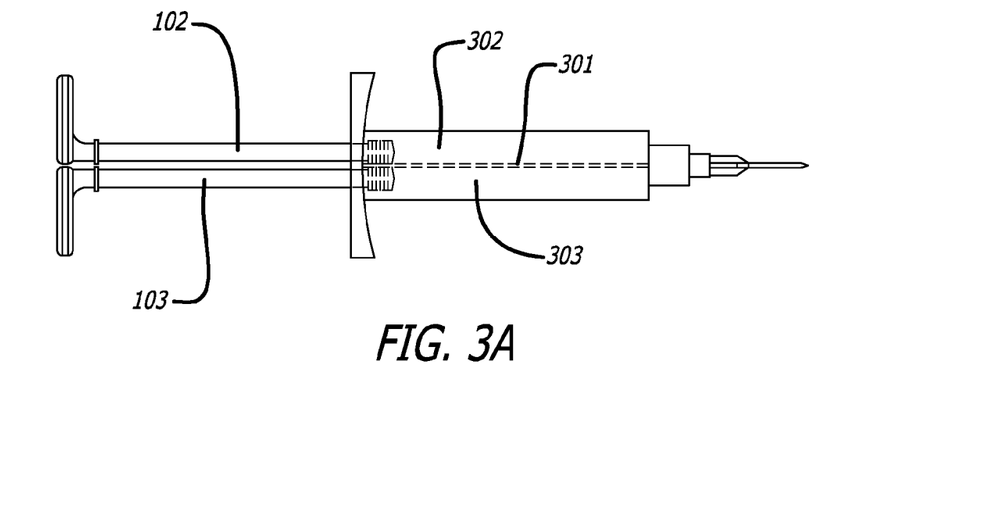
FIGS. 3A-3C illustrate transparent views of an example dual-chamber/dual-plunger syringe in accordance with an example embodiment.
Figure 3B:
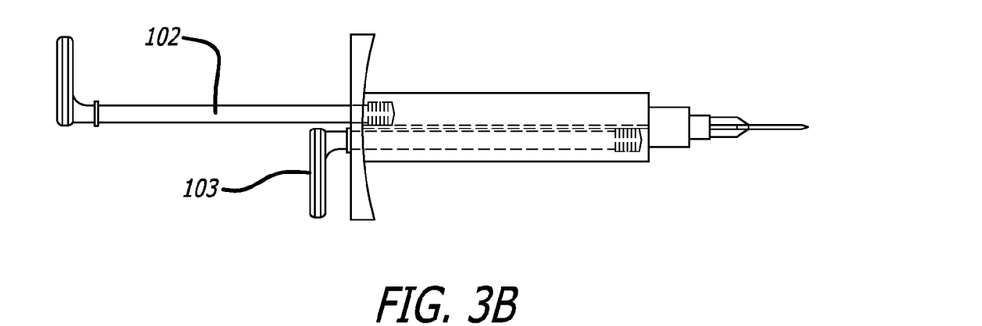
Figure 3C:
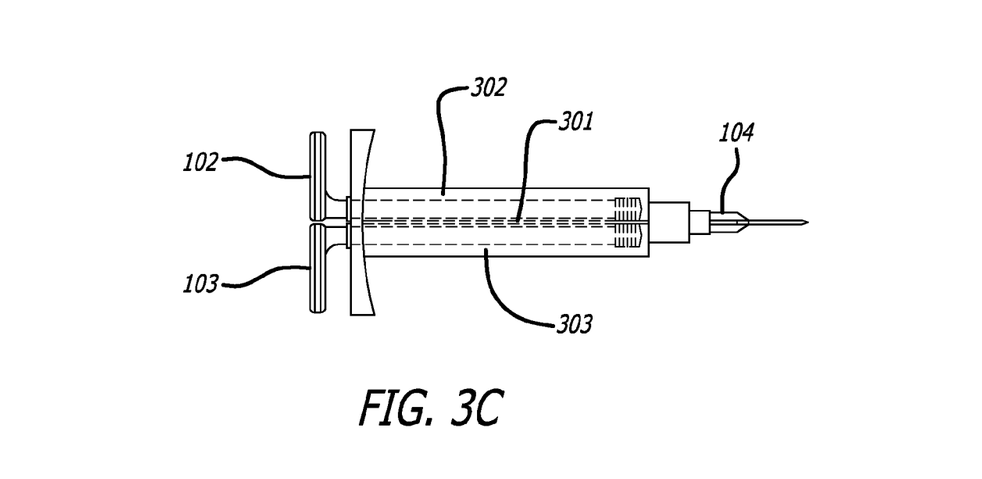

FIGS. 3A-3C illustrate an example embodiment in use in more detail. As an initial matter, the dividing wall 301, and the two chambers 302, 303 may be seen in the transparent view. In the initial state (FIG. 3A) both plungers 102, 103 are fully extended out of the distal end of the syringe body 101. A user may then apply a force to one of the plungers 102, 103, e.g. plunger 103, such as shown in FIG. 3B. As the user pushes the first plunger 103 towards the proximal end of the syringe body 101, material is extruded from the needle 104. Once the first plunger 103 has been pushed its entire length, the user may then begin pushing the second plunger 102, and may push that plunger 102 into the syringe body 101 until the syringe body 101 has been emptied, as shown in FIG. 3C.

In order to facilitate this process, a number of locking devices may be provided. Such locking devices may be necessary to the operation of the syringe device because, during use, the force exerted on each plunger 102, 103 may result in a force tending to push the other plunger 102, 103 out of the syringe body 101. These forces may be understood with reference to FIG. 4.

Figure 4:
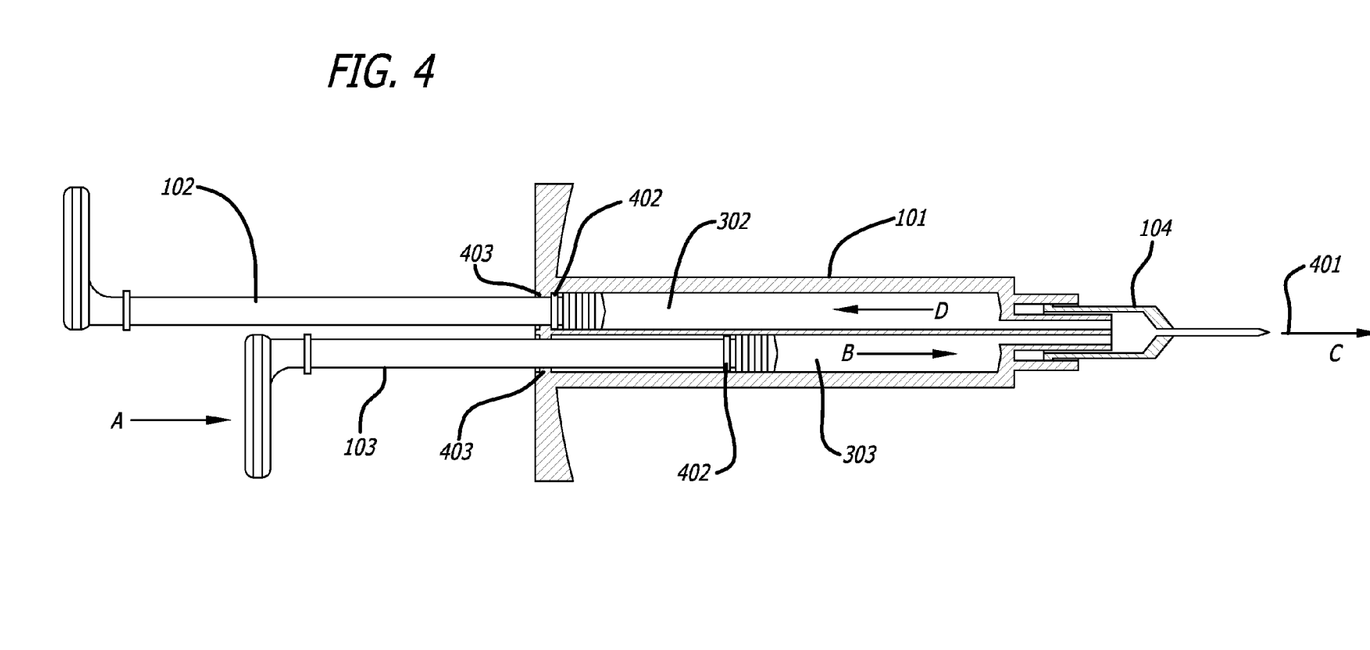
FIG. 4 illustrates a cross-sectional view of a dual-chamber/dual-plunger syringe in accordance with an example embodiment.

First, it is noted that, because, in some embodiments, both chambers 302, 303 of the syringe use the same needle 104, the two chambers 302, 303 are not fully separated, but, rather, are in communication at the proximal end of the syringe. Thus pressure applied to the material in the first chamber 303 is also experienced in the second chamber 302. Locking mechanisms may therefore be provided to keep the plungers 102, 103 in place when experiencing such forces.

For instance, as shown in FIG. 4, a force A is being applied to the lower plunger 103 by a user. As a result, the fluid in the lower chamber 303 exerts a force B to the needle 104, which in turn causes fluid 401 to be extruded through the needle 104, as intended. However, because the two chambers 302, 303 are in communication, the fluid also applies force D to the upper plunger 102. If the upper plunger 102 were free to slide, it could be pushed out of the syringe body 101. Therefore, a locking mechanism may be supplied to prevent the unused plunger from moving.

The locking mechanism may take any appropriate form. For instance, a tab 402, or multiple tabs, may be provided on the plunger rod 102, 103, near the distal end of the plunger rod 102, 103. For example, as illustrated in the drawings, two tabs 402 may be located on the plunger rods 102, 103, opposite from one another. Such tabs 402 may be made of any material, and may be an integral part of the plunger rod 102, 103 or may be attached to the plunger rod 102, 103. In addition, slots 403 may be provided in the body of the syringe 101, corresponding to the position of the tab or tabs 403, when the plungers 102, 103 are in their initial position. For instance, a slot 403 may be provided in the inner surface of the chamber 302, 303 in which the plunger 102, 103 is inserted, near the distal end of the chamber. In the initial state, the tab 403 may be engaged in the slot 403, and may prevent the plunger 102, 103 from sliding out of the syringe body 101.

In some example embodiments, other locking mechanisms may be employed. For example, a tab and slot lock may again be used. However, the tab may be located on the syringe body while the slot is formed in the plunger rod. Alternatively, a tab may again be provided on either element, while another tab or ridge is provided on the corresponding element. For instance, a tab may be provided on the plunger rod, and a second tab may be provided on the syringe. In such a case, the initial position of the plunger rod tab would be closer to the proximal end of the syringe than the tab or ridge on the syringe body.

In addition, the locking mechanism may be structured to be directional. For example, a tab and slot lock may be provided in which both the tab and the slot are triangular, or wedge shaped. For example, a tab formed on the plunger rod may have a triangular cross-section, where the tab joins the plunger rod at an acute angle closer to the proximal end, while the tab joins the plunger rod at a right angle further from the proximal end. Using such a locking mechanism, less force may be needed to push the plunger towards the needle than is required to push the plunger away from the needle when the lock is engaged.

Such locking mechanisms may be provided for both plungers 102, 103, for just one plunger, or for any number of plungers in example embodiments employing more than two plungers. In addition, similar locking mechanisms may be provided for locking plungers in their final position.

Figure 5:
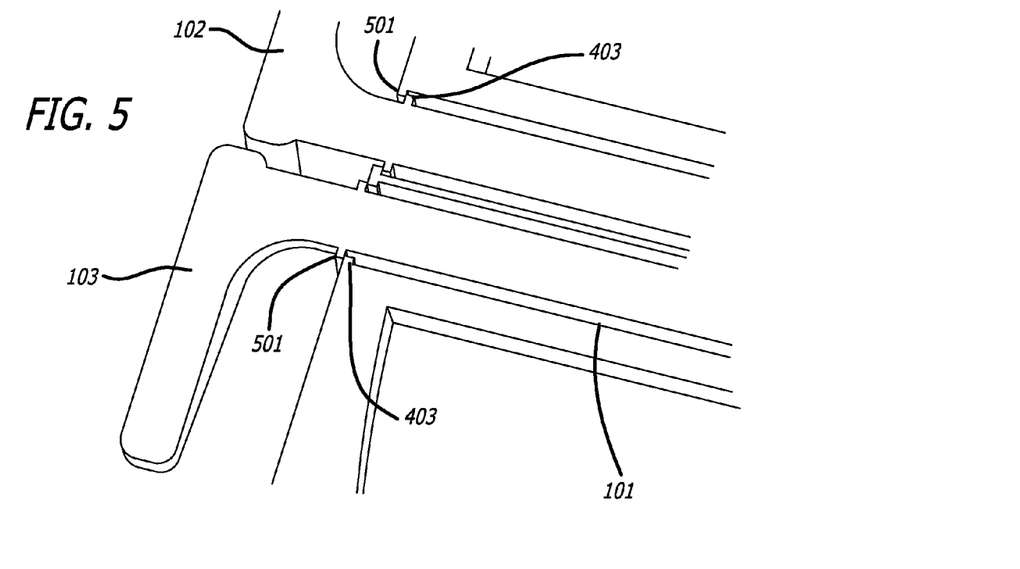
FIG. 5 illustrates a detailed view of an example dual-chamber/dual-plunger syringe in accordance with an example embodiment.

For instance, a second tab 501, illustrated in FIG. 5, may be provided on a plunger rod 102, 103 located closer to the distal end. Such a tab 501 may be shaped to engage with the same slot 403 used, to engage a tab 402 locking the plunger 102, 103 in an initial position. Alternatively, a different slot may be used. Again, any locking mechanism may be employed. For instance, as above, a slot may be provided on the plunger rod 102, 103 while a tab is provided on the syringe body 101.

In FIG. 5, one of the two plungers 102 has been pushed entirely into the syringe 101. In this position, two locking tabs 501 disposed on either side of the plunger rod 102 have engaged in locking slots 403 in the syringe body 101. In this state, the plunger rod 102 will resist further sliding. As can be seen, the other plunger rod 103 has similar locking tabs 501. If the second plunger 103 is pushed slightly further the locking tabs 501 will enter the syringe body 101, align with slots 403 provided in its chamber 303, and, therefore, lock the plunger 103 in its final position as well. At that point all of the material in both chambers 302, 303 may have been extruded.

Figure 6:
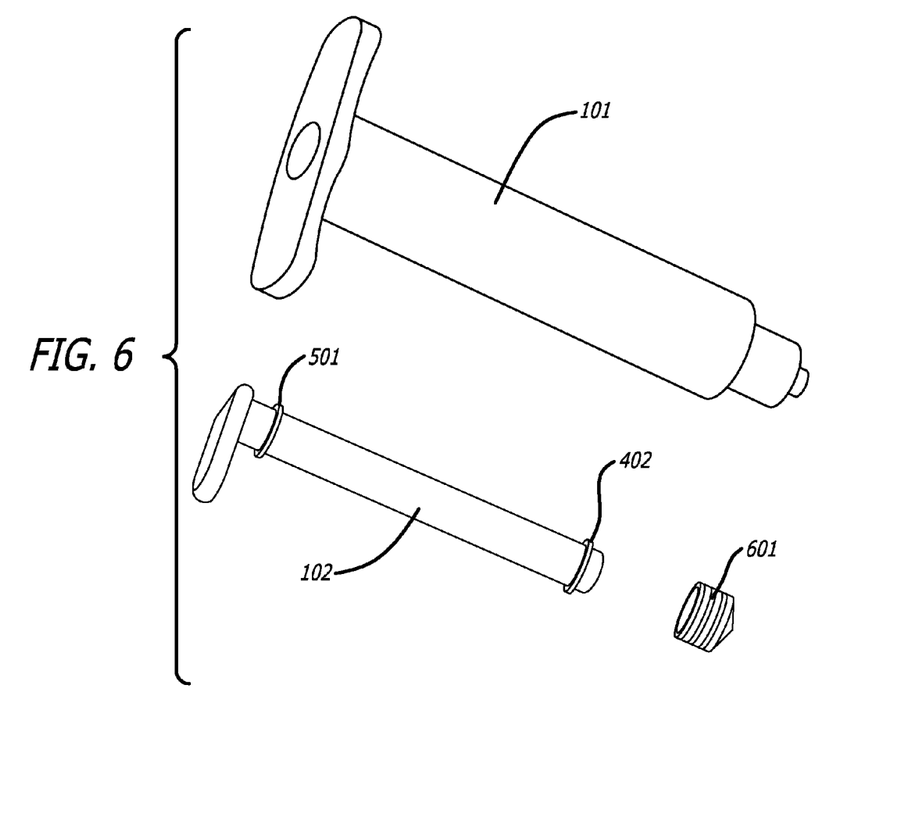
FIG. 6 illustrates a disassembled view of an example dual-chamber/dual-plunger syringe in accordance with an example embodiment.

Components of a dual half-cylinder embodiment are shown in FIG. 6. Illustrated are a dual half-cylinder chamber syringe 101, one of two half-cylinder shaped plunger rods 102, and one of two semi-circular plunger tips 601. As discussed above, the plunger rod 102 may have a number of locking wings or tabs. For instance, the illustrated plunger rod 102 has a first locking wing 402 near the proximal end, which locks the plunger 102 in its initial position, and another locking wing 501 near the distal end, which locks the plunger rod 102 in its final position.

Such example devices may allow for an approximately 50% reduction in extrusion force, as compared to a standard syringe of single-chamber/single-plunger design with the equivalent volume, outer diameter, and length. If necessary, a further reduction in extrusion force can be accomplished by dividing the single chamber into more than two chambers and adding an additional number of corresponding plungers.

Figure 7A:
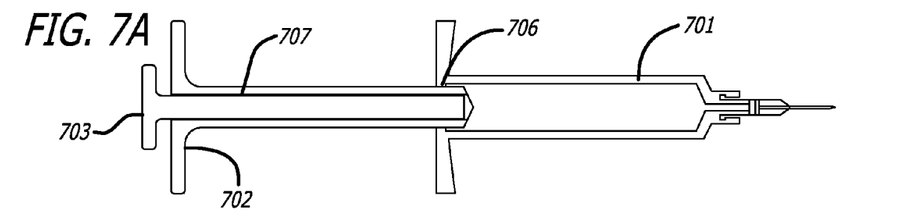
FIGS. 7A-7C illustrate an example single-chamber/dual-plunger syringe in accordance with an example embodiment.
Figure 7B:
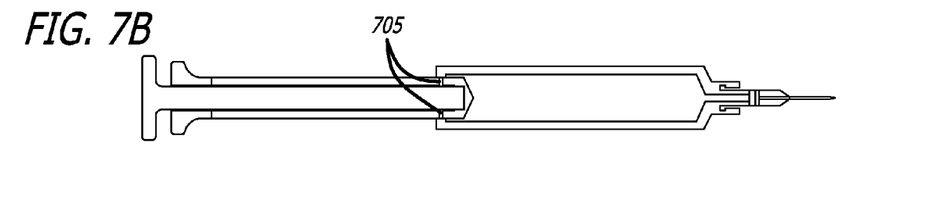
Figure 7C:
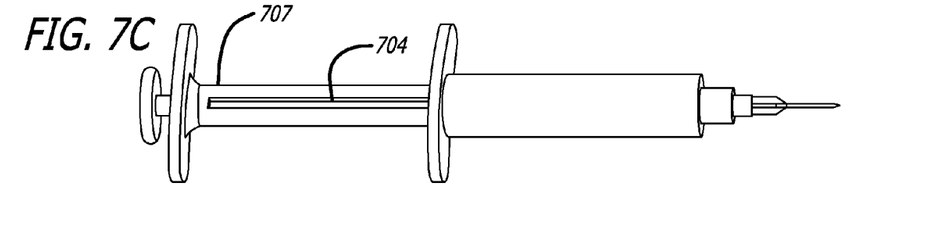
Figure 8A:
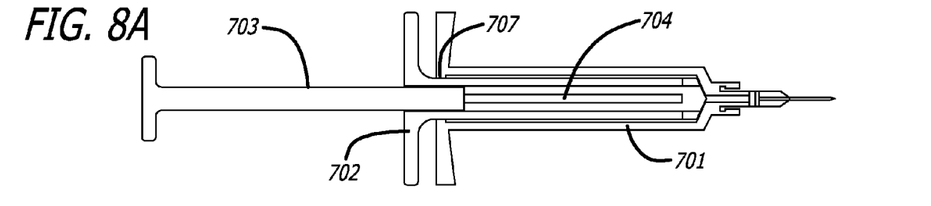
FIGS. 8A-8C illustrate an example single-chamber/dual-plunger syringe in accordance with an example embodiment.
Figure 8B:
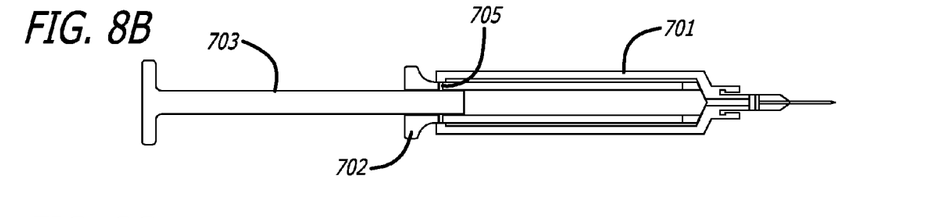
Figure 8C:
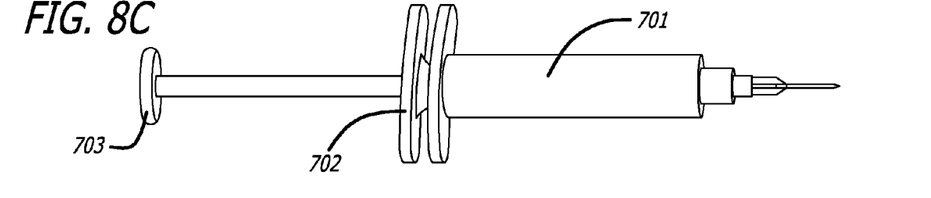
Figure 9A:
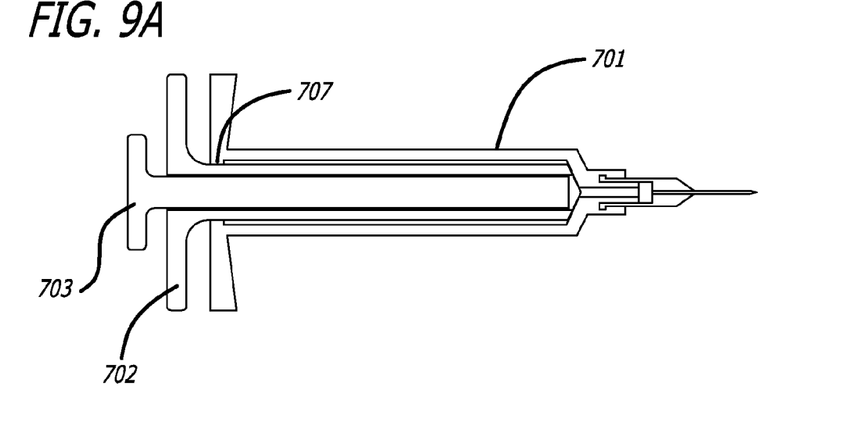
FIGS. 9A-9C illustrate an example single-chamber/dual-plunger syringe in accordance with an example embodiment.
Figure 9B:
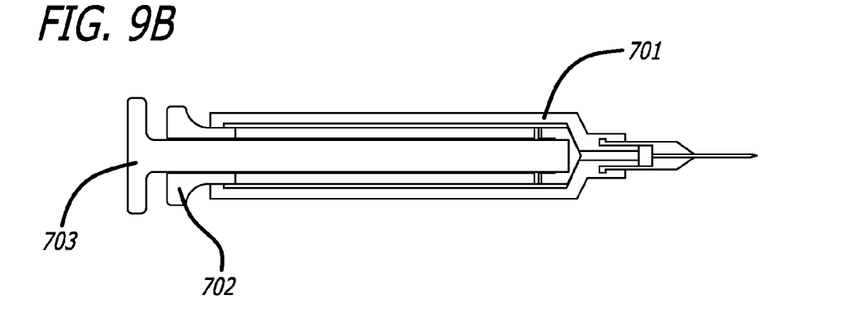
Figure 9C:
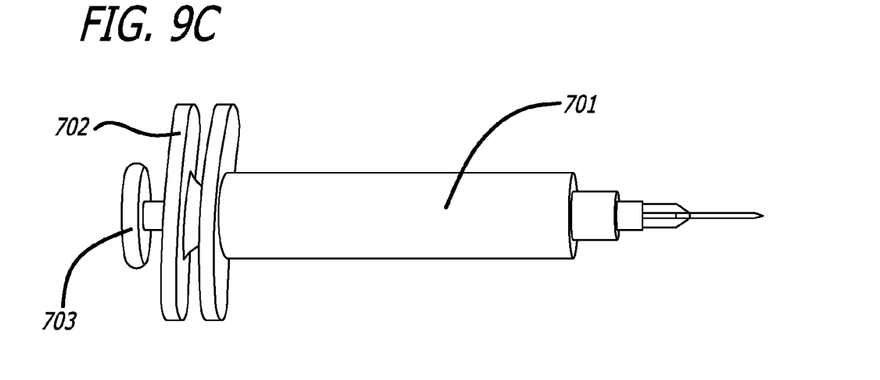

Another example embodiment is illustrated in FIG. 7. The example embodiment again provides a syringe body 701 and two or more plungers 702, 703. In the example embodiment, a syringe 701 with a traditional fluid chamber is used, undivided by a dividing wall. Again two plungers 702, 703 are provided, in the example, an outer 702 and an inner plunger 703. The inner 703 and the outer 702 plungers may be integrated so that they can slide along their common axis, but this motion may be limited between two extreme points. Such plungers 702, 703 may again be essentially in the form of a rod, and may have a plunger tip and a thumb grip. In addition, such plungers 702, 703 may also have any cross-sectional shape. For instance, the plungers 702, 703 are illustrated in the figures with a circular cross-section; however, they may also be elliptical, or have the shape of a rectangle or other polygon.

The example embodiment may again be used by pushing one plunger 702, 703 at a time into the syringe body 701, e.g., the outer plunger 702 may be pressed into the syringe body 701 and then the inner plunger 703 may be likewise pressed into the syringe 701. It is noted that, as in the previous example, exerting a force on the outer plunger 702 may tend to push the inner plunger 703 of the syringe. Accordingly, example embodiments may provide for locking mechanisms to prevent such movement.

As shown in the figure, one or more slots 704 may be provided in the outer plunger rod 702, in the example two slots 704 are provided opposite each other. The slots 704 may extend from a point near the distal end of the plunger shaft, to a point near the proximal end. In addition, one or more locking arms 705 may be provided on the inner plunger rod 703. Again, two locking arms 705 are provided in the illustrated example. A locking groove 706 may be provided in the syringe body 701 which is configured to engage the locking arms 705, when the inner plunger 703 is in the initial position. In order to do so, the locking arms 705 may pass through the slots 704 in the outer plunger rod 702. It is noted that, because the slots 704 may extend along the length of the outer plunger rod 702, the plunger rods 702, 703 may be free to slide relative to each other. It is also noted that, because it is not possible to use the inner plunger 703 first, in the example embodiment, the inner plunger 703 need not be supplied with a locking mechanism preventing movement from its final position. However, in other embodiments such a mechanism may be supplied.

Also as noted above, force exerted on the inner plunger 703 will tend to force the outer plunger 702 out of the syringe 701 as well. Accordingly, the outer plunger 702 may also be provided with a locking mechanism. For example, the outer plunger rod 702 may include one or more locking arms 707, positioned near the distal end of the plunger rod 702. For instance, it may be equipped with two locking arms 707, e.g., at a 90° angle to the locking arms 705 of the inner plunger 703. These locking arms 707 may engage with the same locking groove 706 formed in the syringe 701, or in another groove. Again, as the outer plunger 702 must be used first in the initial configuration, there may be no need to lock it in its initial position. However, some embodiments may provide locking arms, or other mechanisms, for that purpose.

FIGS. 7A-9C illustrate the use of such an example embodiment. In FIGS. 7A-7C, the plungers 702, 703 are in their initial position, as described. From this position a user may apply a force to the outer plunger rod 702, pushing it into the syringe body 701 and extruding material from the needle 708. Force may be applied to the outer plunger 702 until it slides all the way to the other end of the syringe chamber and locks into its final position through the two locking arms 707, in the position shown in FIGS. 8A-8C. The inner plunger 703 may have been held in place by its two locking arms 705, as the outer plunger rod 702 was pressed into the syringe 701, resisting the force exerted by the fluid in the chamber. The outer plunger slots 704 allow for the inner plunger locking arms 705 to engage the syringe groove 706 while the outer plunger moves 702.

Once the outer plunger 702 locks into its final position, force may be applied to the inner plunger 703 until the remaining material is extruded. Once the inner plunger 703 is pushed all the way into the syringe body 701, all of the material in the syringe will have been extruded, and the device will be in its final position, shown in FIG. 9A-9C.

Figure 10:
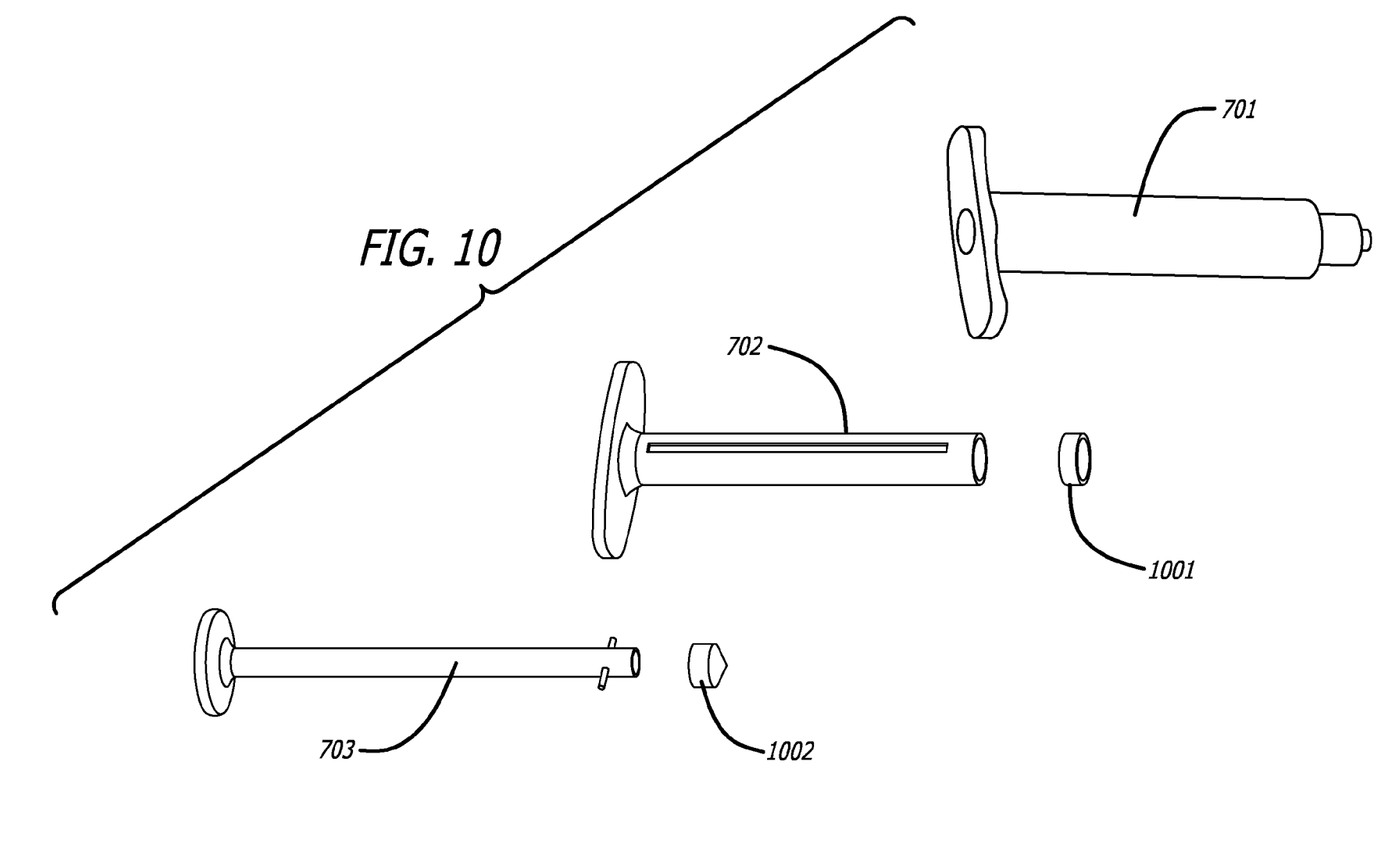
FIG. 10 illustrates a disassembled view of an example single-chamber/dual-plunger syringe in accordance with an example embodiment.

FIG. 10 illustrates example components of such example embodiments, in detail. The figure illustrates a single cylindrical chamber syringe 701, an outer plunger 702 with two slots 704 and two locking arms 707, an outer plunger tip 1001, an inner plunger 703 with two locking arms 705, and an inner plunger tip 1002. As explained above, when assembled, the outer plunger 702 fits into the syringe 701, while the inner plunger 703 fits into the outer plunger 702. The plunger tips 1001, 1002 nest similarly. For example, the outer plunger tip 1001 may be shaped in the form of a ring, while inner plunger tip 1002 may be shaped in the form of a disk, able to fit within the outer plunger tip 1001.

Such example embodiments may also allow for an approximately 50% reduction in extrusion force, as compared to a standard syringe of single-chamber/single-plunger design with the equivalent volume, outer diameter, and length.

In the preceding specification, the present invention has been described with reference to specific example embodiments thereof. It will, however, be evident that various modifications and changes may be made thereunto without departing from the broader spirit and scope of the present invention. The description and drawings are accordingly to be regarded in an illustrative rather than restrictive sense.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A syringe, comprising:
a syringe body with a fluid chamber;
a dividing wall disposed within the fluid chamber, defining a first fluid chamber and a second fluid chamber, the first fluid chamber and the second fluid chamber in communication with the extrusion opening;
the first chamber and the second chamber containing a dermal filler gel;
a first plunger disposed in the first chamber and slidable between an initial position and a final position; and
a second plunger disposed in the second chamber and slidable between an initial position and a final position, the second plunger including a locking mechanism configured to prevent the second plunger from being pushed out of the syringe body when the first plunger is being depressed from its initial position to its final position during dispensing of the dermal filler gel from the first chamber and out of the extrusion opening;
wherein the first plunger includes a locking mechanism configured to prevent the first plunger from sliding away from its final position, when the second plunger is being depressed from its first position to its second position during dispensing of the dermal filler gel from the second chamber and out of the extrusion opening.

2. The syringe of claim 1, wherein the locking mechanism of the first plunger comprises:
a tab on the first plunger; and
a groove formed in the first fluid chamber;
wherein the tab is positioned to engage in the groove when the first plunger is in its final position.

3. The syringe of claim 1, wherein the locking mechanism of the second plunger comprises:
a tab on the second plunger; and
a groove formed in the second fluid chamber;
wherein the tab is positioned to engage in the groove when the second plunger is in its initial position.

4. A dermal filler syringe, comprising:
a syringe body with a fluid chamber;
a dividing wall disposed within the fluid chamber, defining a first fluid chamber and a second fluid chamber, the first fluid chamber and the second fluid chamber in communication with the extrusion opening;
both of the first chamber and the second chamber containing a dermal filler gel;
a first plunger disposed in the first chamber and slidable between an initial fully extended position and a final fully inserted position; and
a second plunger disposed in the second chamber and slidable between an initial fully extended position and a final fully inserted position;
the second plunger including a locking mechanism configured to prevent the second plunger from being pushed out of the syringe body when the first plunger is being depressed from its initial fully extended position to its final fully inserted position during dispensing of the dermal filler gel from the first chamber and out of the extrusion opening; and
the first plunger including a locking mechanism configured to prevent the first plunger from sliding away from its final fully inserted position when the second plunger is being depressed from its first fully extended position to its second fully inserted position during dispensing of the dermal filler gel from the second chamber and out of the extrusion opening.

5. The dermal filler syringe of claim 4, wherein the locking mechanism of the first plunger comprises:

a tab on the first plunger; and a groove formed in the first fluid chamber;

wherein the tab is positioned to engage in the groove when the first plunger is in its final fully inserted position.

6. The dermal filler syringe of claim 4, wherein the locking mechanism of the second plunger comprises:

a tab on the second plunger; and a groove formed in the second fluid chamber;

wherein the tab is positioned to engage in the groove when the second plunger is in its initial fully extended position.

* * * * *